(12) United States Patent
Li et al.

(10) Patent No.: US 8,821,917 B2
(45) Date of Patent: Sep. 2, 2014

(54) BIOPOLYMERIC MEMBRANES

(75) Inventors: Shu-Tung Li, Oakland, NJ (US); Debbie Yuen, Woodcliff Lake, NJ (US); Peggy Hansen, Mahwah, NJ (US)

(73) Assignee: Collagen Matrix, Inc., Oakland, NJ (US)

( * ) Notice: Subject to any disclaimer, the term of this patent is extended or adjusted under 35 U.S.C. 154(b) by 0 days.

(21) Appl. No.: 12/897,155

(22) Filed: Oct. 4, 2010

(65) Prior Publication Data

US 2011/0021754 A1  Jan. 27, 2011

Related U.S. Application Data

(62) Division of application No. 10/971,435, filed on Oct. 22, 2004, now Pat. No. 7,807,192.

(51) Int. Cl.
*A61F 13/00* (2006.01)
*C07K 14/78* (2006.01)
*B29C 67/00* (2006.01)
*B29C 67/24* (2006.01)

(52) U.S. Cl.
USPC ............ 424/443; 530/356; 264/319; 264/330

(58) Field of Classification Search
None
See application file for complete search history.

(56) References Cited

U.S. PATENT DOCUMENTS

| | | |
|---|---|---|
| 4,349,026 A | 9/1982 | Miyata |
| 4,725,671 A | 2/1988 | Chu et al. |
| 4,963,146 A | 10/1990 | Li |
| 5,206,028 A | 4/1993 | Li |
| 5,512,291 A | 4/1996 | Li |
| 6,110,590 A | 8/2000 | Zarkoob et al. |
| 6,179,872 B1 | 1/2001 | Bell et al. |
| 6,391,333 B1 | 5/2002 | Li et al. |
| 6,592,623 B1 | 7/2003 | Bowlin et al. |
| 2004/0001877 A1 | 1/2004 | Li et al. |
| 2004/0037813 A1 | 2/2004 | Simpson et al. |
| 2004/0110439 A1 | 6/2004 | Chaikof et al. |
| 2005/0181977 A1 | 8/2005 | Hunter et al. |

OTHER PUBLICATIONS

Oneson et al., "The Preparation of Highly Purified Insoluble Collagens", Journal of the American Leather Chemists Association 65:440-450, 1970.

Yuen et al., "A Resorbable, Reconstituted Type I Collagen Membrane for Guided Tissue Regeneration and Soft Tissue Augmentation", Transactions of the Sixth World Biomaterials Congress p. 1288, 2000.

Chvapil, M. et al., "Collagen fibers as a temporary scaffold for replacement of ACL in goats" Journal of Biomedical Materials Research, Mar. 1993, vol. 27, No. 3, pp. 313-325.

*Primary Examiner* — Patricia A Duffy
*Assistant Examiner* — Garen Gotfredson
(74) *Attorney, Agent, or Firm* — Cesari and McKenna, LLP

(57) ABSTRACT

This invention relates to a sheet membrane for repairing a damaged tissue. The membrane includes an isotropic layer of cross-linked biopolymeric fibers in which the fibers are 10 to 1,000 cm in length. This invention also relates to a method of making an isotropic layer of cross-linked biopolymeric fibers. The method includes: (1) coacervating biopolymeric fibers (e.g., collagen-based fibers) having lengths of less than 1 cm dispersed in an aqueous solution to obtain coacervated biopolymeric fibers having lengths of 10 to 1,000 cm; (2) flattening the coacervated biopolymeric fibers into a layer; (3) drying the layer; and (4) cross-linking the biopolymeric.

10 Claims, No Drawings

BIOPOLYMERIC MEMBRANES

CROSS-REFERENCE TO RELATED APPLICATIONS

This application is a divisional application of U.S. application Ser. No. 10/971,435 filed on Oct. 22, 2004, the contents of which are hereby incorporated by reference in its entirety.

BACKGROUND

Biopolymeric membranes can be used in soft tissue repair. See, e.g., Shu-Tung Li, Biologic Biomaterials Tissue-Derived Biomaterials (Collagen). In: *Biomedical Engineering Handbook*, Ed. J. D. Bronzino, 42-1 to 42-23, CRC Press, Inc. Boca Raton, Fla., 2000. Mechanical strength is an important consideration in designing such membranes as there is a need for securely affixing them to target sites.

SUMMARY

This invention is based on an unexpected discovery that biopolymeric membranes containing long unoriented fibers have high tensile strength and high suture retention strength in all directions.

In one aspect, this invention features a sheet membrane for repairing a damaged tissue. The sheet membrane includes an isotropic layer of cross-linked biopolymeric fibers in which the fibers are 10 to 1,000 cm (e.g., 30 to 800 cm or 50 to 500 cm) in length. The length refers to the average of the fiber lengths measured before the fibers are cross-linked and has a standard deviation of ±20%.

The biopolymeric fibers can be based on a variety of biopolymers, such as polypeptides (e.g., type I to type XXV collagen, elastin, and fibrin), polysaccharide (e.g., chitosan, alginic acid, cellulose, and glycosaminoglycan), and a combination of two or more different biopolymers. The biopolymers are either obtainable from natural sources or prepared by genetic engineering techniques. The term "isotropic layer" refers to a layer that exhibits properties with similar mechanical properties when measured along axes of all directions. The isotropic layer can have a thickness of 0.05 to 1.5 mm (e.g., 0.2 to 0.8 mm), a density of 0.1 to 1.2 g/cm$^3$ (e.g., 0.2 to 1.0 g/cm$^3$), a hydrothermal transition temperature of 45 to 80° C. (e.g., 50 to 70° C.), a suture retention strength of 0.1 to 5 kg (e.g., 0.2 to 2 kg), and a tensile strength of 20 to 250 kg/cm$^2$ (e.g., 40 to 100 kg/cm$^2$). Preferably, it is permeable to molecules having molecular weights of 50 to 100,000 daltons (e.g., 100 to 70,000 daltons). The above parameters can be readily measured by methods well known in the art, some of which are described in greater detail below. If desired, one can include in the isotropic layer a bioactive agent, such as growth factors, anti-microbial agents, anti-clotting agents, and anti-adhesive agents.

In another aspect, this invention features a method of making an isotropic layer of cross-linked biopolymeric fibers. The method includes 4 steps: (1) coacervating biopolymeric fibers (e.g., collagen-based fibers) having lengths of less than 1 cm dispersed in an aqueous solution to obtain coacervated biopolymeric fibers having lengths of 10 to 1,000 cm, (2) flattening the coacervated biopolymeric fibers into a layer, (3) drying the layer, and (4) cross-linking the biopolymeric fibers. Coacervation can be achieved by adjusting the pH of the dispersion to the isoelectric point of the biopolymer. As a result, the biopolymer is precipitated from the dispersion and forms long fibers (e.g., having lengths of 10 to 1,000 cm).

Preferably, the coacervated fibers are partially dehydrated to reach a solid content of 5-25 wt % before step (2).

Also within the scope of this invention is an isotropic layer of cross-linked biopolymeric fibers prepared by the method mentioned above.

The details of one or more embodiments of the invention are set forth in the accompanying description below. Other features, objects, and advantages of the invention will be apparent from the description and from the claims.

DETAILED DESCRIPTION

This invention relates to a sheet membrane containing an isotropic layer of long cross-linked biopolymeric fibers. Below is an example of preparing such a sheet membrane from type I collagen:

First, type I collagen fibers are purified from a natural source (e.g., skin, bone, tendon, or ligament of a mammal) by methods well known in the art (e.g., those disclosed in U.S. Pat. No. 5,206,028 and in Oneson, et al., *J. Am. Leather Chemists Assoc.* 65:440-450, 1970).

Next, a collagen dispersion is prepared by mixing purified type I collagen fibers in an acidic or basic aqueous solution in which fibers do not cross-link with each other. For example, one can disperse collagen fibers in an acidic aqueous solution containing either an organic acid (e.g., acetic acid or lactic acid) or an inorganic acid (e.g., hydrochloric acid or sulfuric acid). The solid content of collagen fibers in the dispersion preferably ranges from 0.5 wt % to 15 wt %. Alternatively, one can disperse collagen fibers in a basic aqueous solution containing a base such as sodium hydroxide, potassium hydroxide, or calcium hydroxide. Methods for preparing a collagen dispersion are well known in the art. See, e.g., U.S. Pat. No. 5,206,028. Typically, collagen is first homogenized in an acidic or basic solution by a suitable means, such as using a blender. The collagen dispersion thus obtained is then filtered to remove any residual non-collagenous materials, such as by passing the dispersion through a stainless steel mesh filter of a suitable mesh size. The fibers in the filtered dispersion are generally less than 1 cm in length.

The collagen fibers in the filtered dispersion are then coacervated to obtain long fibers of certain lengths (e.g., 10 to 1,000 cm). This can be achieved by adjusting the pH of the dispersion to the isoelectric point of the collagen (e.g., pH of about 5). Either a base or an acid can be used as a coacervating agent, depending upon whether the collagen fibers are dispersed in an acid or alkaline solution. Other coacervating agents (e.g., neutral salts or non-aqueous solvents) can also be used. The lengths of coacervated fibers in their extended conformation are measured to ensure that fibers of desired lengths are obtained. Typically, coacervated fibers are placed on a surface with a dark background and their lengths are measured with a ruler. If the desired lengths are not obtained, vacuum can be applied to the coacervated fibers to remove trapped air bubbles that interfere with the fiber alignment. Removing trapped air bubbles elongates fibers by improving adhesion between adjacent fibers. This process can be repeated until the lengths of fibers are within the range of 10-1,000 cm. The desired lengths can also be obtained by adjusting the total amount of the dispersion used in the coacervation process.

The coacervated collagen fibers are substantially collected from the solution, e.g., using a mesh screen. Preferably, the fibers are partially dehydrated either by dripping or by squeezing in a stainless steel mesh holder to reach a solid collagen content in the range of 5% to 25% by weight. The fibers thus obtained are randomly oriented and possess dough-like properties. They can be conveniently flattened with a roller into a sheet membrane containing an isotropic layer of collagen fibers. While some collagen fibers in the sheet membrane are in a more extended conformation, most are in a coiled or bent conformation.

The sheet membrane thus obtained is then dried. Drying can be carried out by either air-drying or freeze-drying, depending upon the desired permeability of the membrane. In general, air-drying produces a membrane allowing permeation of molecules having molecular weights ranging from 50 to 30,000 (e.g., ions and small peptides), and freeze-drying produces a membrane allowing permeation of molecules having molecular weights ranging from 1,000 to 100,000 (e.g., various growth factors and bioactive macromolecules). Permeability of a sheet membrane can be further adjusted by controlling the extent of partial dehydration mentioned above. Methods for determining permeability of a sheet membrane are well known in the art. See, e.g., Li, et al., *Clinical Materials*, 9:195-200, 1992.

Note that the permeability of a sheet membrane is much lower than the permeability of a porous, sponge-like structure. Generally, for a collagen sponge having a density in the range of 0.005 to 0.02 g/cm$^3$ (such as DuraGen and Helistat marketed by Integra LifeSciences, Plainsboro, N.J.), the majority of pores in the sponge have diameters ranging from 50 to 250 As a result, a collagen sponge allows permeation of cells. See Doillon, et al. *J. Biomed. Materials Res.* 20:1219-1228, 1986. Because of its porous structure, a collagen sponge facilitates cellular ingrowth. A collagen sponge typically contains spherical pores, and its pore size (which corresponds to permeability) can be determined by scanning electron microscopy (SEM).

A collagen sheet membrane of this invention does not have spherical porous structures. It typically has a laminated, multi-layered structure of a high density (e.g., 0.1 to 1.2 g/cm$^3$), and can be produced by mechanical compression (e.g., flattening) as described above. As the spaces between collagen fibers collapse during compression, a collagen sheet membrane may contain surface morphology of pore-like defects (e.g., shallow depth), inter-layer gaps, or slits, not porous structures contained in a collagen sponge. Given its laminated structure, a sheet membrane can be used as a molecular sieve or as a cell barrier (e.g., those disclosed in U.S. Pat. Nos. 5,206,028 and 6,391,333). As an example, U.S. Pat. No. 4,963,146 discloses a laminated multi-layered tubular membrane prepared by mechanical compression of coacervated, hydrated oriented collagen fibers. The membrane is only permeable to macromolecules of the size of bovine serum albumin (having a molecular weight of about 67,000 daltons), but not permeable to macromolecules of the size of β-galactosidase (having a molecular weight of about 5.4×10$^5$ daltons). It also discloses that the permeability of the membrane correlates with the Stokes radius of the macromolecule in an aqueous environment (e.g., 0.007 μm for bovine serum albumin and 0.02 μm for β-galactosidase). Thus, the permeability of a sheet membrane (e.g., permeable to biomolecules smaller than 0.02 μm) can be much lower than that of a sponge (e.g., permeable to cells of about 50 μm). Given its low permeability, a sheet membrane can be used to exchange nutrients while excluding cells at the same time. The permeability of a sheet membrane can be determined by using probe molecules, i.e., macromolecules having various molecular sizes. See, e.g., Li, et al., *Clinical Materials*, 9:195-200, 1992. As a sheet membrane does not contain spherical pores, its permeability cannot be determined by measuring the pore size using SEM.

The dried sheet membrane mentioned above is then subjected to reaction with a suitable cross-linking agent (e.g., an aldehyde compound). It can be cross-linked in a solution containing a cross-linking agent, with the extent of cross-linking being controlled by the concentration of the cross-linking agent, the temperature and pH of the solution, and the reaction time. Alternatively, the dried membrane can be cross-linked in a vapor generated from a solution containing a cross-linking agent, with the extent of cross-linking being controlled by the vapor pressure, the solution temperature, and the reaction time. Methods for determining the extent of cross-linking are well known in the art, e.g., by monitoring the hydrothermal transition temperature or by determining the number of intermolecular cross-linking points. See Yuen, et al., *Trans. Soc. Biomaterials*, 1288, 2000 and Wiederhorn, et al., *J. Polymer Sci.*, 9:315, 1952.

The extent of cross-linking determines the in vivo stability of a sheet membrane. For example, collagen fibers with a hydrothermal transition temperature of 50° C. to 55° C. and 55° C. to 60° C. can have a complete resorption time in vivo of 8 to 16 weeks and 12 to 36 weeks, respectively. See Yuen, et al., *Trans Soc. Biomaterials*, 1288, 2000. For in vivo stability greater than 6 months, the hydrothermal transition temperature should be tailored to the range of 55° C. to 75° C.

The cross-linked membrane thus obtained can be rinsed extensively with distilled water to remove any residual aldehyde, thereby rendering the membrane non-cytotoxic. The rinsed membrane can then be freeze-dried to produce a white sheet membrane. White color is preferred as it facilitates precise placement of a sheet membrane onto a repair site. The freeze-drying can be carried out at or below −40° C. if the membrane is air-dried before cross-linking. As the freezing point depression of protein-bound water is more pronounced in a cross-linked air-dried membrane (i.e., a high density material), the water absorbed in the cross-linked membrane may not completely freeze at a temperature above −40° C. during the freeze drying cycles. Thus, freeze-drying a cross-linked air-dried membrane at a higher temperature (e.g., −10° C.) may produce membranes with transparent patches similar to those produced by air drying.

In vivo stability of a sheet membrane also depends on the types of cross-linking agents. Generally, glutaraldehyde forms more stable membranes than formaldehyde or carbodiimide. Thus, glutaraldehyde has been used to cross-link tissue heart valves that require high in vivo stability, while formaldehyde has often been used to cross-link resorbable implants whose in vivo stability is less critical.

If desired, a sheet membrane can include one or more bioactive agents. For example, a bioactive agent can be dissolved or dispersed in a collagen dispersion used to prepare the sheet membrane. As another example, bioactive molecules can be covalently linked to the surface of collagen fibers in a sheet membrane. Specifically, a bioactive molecule containing a reactive group can be linked via a coupling agent to a functional group on the side chains of collagen. Examples of such a suitable coupling agent include aldehyde or carbodiimide compounds. Examples of such a functional group include the side-chain amino groups in lysines and hydroxylysines, the side-chain carboxyl groups in aspartic and glutamic acids, and the side-chain hydroxyl groups in hydroxyproline, serines, and threonines. See, e.g., Lundblad R., *Techniques in protein modification*, CRC Press, Boca Raton, 1995. In addition, spacer molecules can be used to form links between the functional groups on the side chains of collagen and the reactive groups on the bioactive molecules so as to confer more flexibility on such bioactive molecules on the surface of the membrane.

A sheet membrane of this invention contains an isotropic layer of long cross-linked biopolymeric fibers. As a result, it provides enhanced suture retention strength and tensile strength in all directions. By contrast, a sheet membrane containing oriented fibers provides high suture retention strength and tensile strength only in certain directions. See Example 5 below. Specifically, a sheet membrane containing oriented fibers has higher suture retention strength in the direction perpendicular to the fiber orientation than in the direction parallel to the fiber orientation. On the other hand, it has higher tensile strength in the direction parallel to the fiber orientation than in the direction perpendicular to the fiber orientation. Since it is difficult to discern the fiber orientation in a sheet membrane containing oriented fibers, failure may occur if the sheet membrane is not properly placed in a target site.

A sheet membrane of this invention can be used in soft tissues repair. For example, when used in repairing of a pericardium tissue after open-heart surgery, the membrane provides uniform strength in all directions such that it can be sutured with the host pericardium to prevent tear and to protect the tissue. As another example, when used in repairing hernia of the abdominal-wall, it provides uniform strength to support the herniated tissue. A sheet membrane of this invention can also be used in gastric and lung surgeries.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Preparation of Purified Collagen Fibers

Bovine deep flexor tendon was used to prepare type I collagen fibers. Initially, the fat and fascia of the tendon were carefully removed and washed with water. The tendon thus obtained contained mostly type I collagen fibers and was subsequently frozen and comminuted into 0.5 mm slices with a meat slicer. 1 kg of sliced wet tendon was first extracted in 5 liters of distilled water at room temperature for 24 hours. The extractant was discarded. A 5-liter solution containing 0.2 N HCl and 0.5 M $Na_2SO_4$ was added and the tendon slices were extracted at room temperature for 24 hours. After decantation of the acidic extractant, the tendon was washed with 5 liters of a 0.5 M $Na_2SO_4$ solution to remove the residual acid. The acid extracted tendon was then extracted in a 5-liter solution containing 0.8 M NaOH and 1 M $Na_2SO_4$ at room temperature for 24 hours. The basic extractant was then discarded. The residual base was neutralized with a 0.5 N HCl solution to pH 5, followed by several changes of distilled water to remove the residual salts associated with the tendon. The tendon was then defatted with isopropanol (tendon:isopropanol=1:5, v/v) for 8 hours at 25° C. After decantation of the extractant, an equal volume of isopropanol was added and the tendon slices were extracted overnight at 25° C. The defatted tendon was then equilibrated in a 0.05 M phosphate buffer solution, pH 7.4 for 24 hours. The excess buffer solution was decanted and the purified collagen fibers were stored wet in a freezer at a temperature lower than −20° C. or stored in the air-dried form at room temperature.

EXAMPLE 2

Preparation of Collagen Fiber Dispersions

An aliquot of purified collagen fibers was weighed and dispersed in a 0.07 M lactic acid solution. The dispersion thus obtained was homogenized with a Silverson Homogenizer (Silverson Machines, Inc., East Longmeadow, Mass.). The homogenization was carried out for about 1 to 3 minutes. The homogenized dispersion was then filtered with a 40 mesh stainless steel mesh filter. The filtered dispersion, which had a collagen content of 0.62% (w/v), was de-aerated with vacuum to remove trapped air.

EXAMPLE 3

Fabrication of a Sheet Membrane from Dispersed Collagen Fibers Via Freezing-drying 1.5 kg of the collagen fiber dispersion prepared in Example 2 (0.62%) was added into a 4 liter flask. The collagen fibers were coacervated by adding 200 ml of a 0.3% $NH_4OH$ solution to adjust the pH of the dispersion to the isoelectric point of collagen (pH of about 5.0).

The coacervated collagen fibers were removed from the beaker and placed in a 20 mesh stainless steel screen. The excess solution was removed by slowly moving the coacervated fibers back and forth with a teflon spatula until the solid content of the hydrated fibers reached between 10% to 15% by weight. The coacervated, partially dehydrated fibers, i.e., collagen dough, were then evenly distributed on a flat plat and flattened with a roller to form a sheet membrane, which was generally rectangular in shape. The membrane covered an area of about 150 $cm^2$, and had a thickness of about 0.3-0.4 mm (measured by a height gauge). The average length of the fibers was about 350±70 cm. The flattened, wet membrane was then freeze-dried at −10° C. for 24 hours and 20° C. for 10 hours under a pressure less than 200 millitorr using a Virtis Freeze Dryer (Virtis, Gardiner, N.Y.). The freeze-dried membrane was cross-linked with formaldehyde vapor generated from a 2% formaldehyde solution at 20° C. for 6 hours. The cross-linked membrane was extensively rinsed with distilled water to remove any residue formaldehyde. It was then freeze-dried again at −10° C. for 24 hours and 20° C. for 10 hours to obtain a white sheet membrane. The sheet membrane thus obtained was then cut into various sizes and shapes (e.g., squares, rectangles, or circles) depending on the desired applications. For example, it can be cut into sizes of from 6.25 $cm^2$ to 125 $cm^2$ for dura mater repair.

EXAMPLE 4

Fabrication of a Sheet Membrane from Dispersed Collagen Fibers Via Air-drying Followed by Freeze-drying 1.5 kg of the collagen fiber dispersion prepared in Example 2 (0.62%) was added into a 4 L flask. Collagen fibers were coacervated by adding 250 ml of a 0.3% $NH_4OH$ solution to adjust the pH of the dispersion to about 5.0. The coacervated collagen fibers were removed from the flask and placed in a 20 mesh stainless steel screen. The excess solution was removed by slowly moving the coacervated fibers back and forth with a teflon spatula until the solid content of the hydrated fibers reached between 10% to 15% by weight. The coacervated, partially dehydrated collagen fibers were then evenly distributed on a flat plate and flattened with a roller to form a sheet membrane. The membrane covered an area of about 150 cm² and had a thickness of 0.45-0.55 mm (measured by a height gauge). The average length of the fibers was about 350±70 cm. The flattened, wet membrane was air-dried in a clean hood. The air-dried sheet membrane was then cross-linked in a 0.8% formaldehyde solution (having a pH of 7) at room temperature for 8 hours. The cross-linked sheet membrane was extensively rinsed with distilled water to remove any residual formaldehyde. It was then freeze-dried at −40° C. for 24 hours and 20° C. for 10 hours to obtain a white membrane sheet.

EXAMPLE 5

Characterization of Sheet Membranes

Six properties (i.e., thickness, density, hydrothermal transition temperature, suture tension strength, tensile strength, and permeability) of four sheet membranes were measured. Specifically, a sheet membrane prepared from Example 3, a sheet membrane prepared from Example 4, a sheet membrane prepared according to U.S. Pat. No. 6,391,333, and a sheet membrane prepared according to U.S. Pat. No. 5,206,028 were studied in this example.

A. Thickness

The thickness of a sheet membrane was determined with a caliper.

B. Density

When determining the density (g/cm³) of a sheet membrane, the membrane was first dried under vacuum for 24 hours or over $P_2O_5$ for 24 hours and the dry weight was recorded. The dimensions (i.e., the length, width, and thickness) of the membrane were then measured using a caliper. The density was determined by the amount of collagen per unit volume of the membrane.

C. Hydrothermal Transition Temperature

For each sheet membrane, a portion having a diameter of 2.5 mm was punched out, hydrated in phosphate buffered saline (PBS), placed in an aluminum cell, and sealed. The sample was then placed in a sample holder of a differential scanning calorimeter (Mettler/Toledo DSC882, Mettler-Toledo Inc., Columbus, Ohio) and heated at a rate of 5° C. per minute. The hydrothermal transition temperature was taken as the peak temperature of the transition from the natural structure of extended collagen fibers to a denatured shrunken structure of the fibers.

D. Mechanical Strength

Suture retention strength: For each sheet membrane, the suture retention strength of a wet membrane was determined using a mechanical tester (Chatillon, Greensboro, N.C.). The membrane was cut to a size of 20 mm×15 mm and soaked in a PBS solution, pH 7.4 at 25° C., for about 5 minutes. A suture (3-0 silk black braided, taper SH-1, Ethicon, Somerville, N.J.) was placed through the 20 mm side at approximately 4 mm from the edge. The suture was tied into a knot and was secured to a hook adapter of the mechanical tester. The membrane was then secured with a clamp at the opposite side of the suture. The suture was pulled at a speed 1.0 in/min until the membrane was pulled apart.

Tensile strength: For each sheet membrane, the tensile strength of a wet membrane was determined using the just-mentioned mechanical tester (Chatillon, Greensboro, N.C.). The membrane was cut into a dumbbell shape with a die punch. The membrane was then soaked in a PBS solution, pH 7.4, at 25° C. for about 5 minutes. It was then secured to a clamp fixture at both ends, and pulled at a speed 1.0 in/min until the membrane was pulled apart.

E. Permeability

For each sheet membrane, a 2-cm diameter disk cut from a sheet membrane was inserted into a hole between two compartments of a specially designed chamber, thereby completely separating the two compartments. A fixed volume of PBS containing 50 µg/ml of various sizes of peptide and protein molecules was added to one compartment. The other compartment was filled with a fixed volume of PBS only. The solutions in both compartments were allowed to equilibrate for 24 hours. An assay was then conducted to determine the sizes of the peptide and protein molecules in the compartment which initially only contained PBS.

The experimental results were summarized in Table 1 below. Unexpectedly, these results showed that the sheet membranes prepared from Examples 3 and 4 (i.e., containing unoriented long fibers) had high suture retention strength and high tensile strength in two perpendicular directions. A membrane prepared according to U.S. Pat. No. 6,391,333 (i.e., containing oriented fibers) had high suture retention strength or high tensile strength only in one direction (either perpendicular to the fiber orientation or parallel to the fiber orientation). Further a membrane prepared according to U.S. Pat. No. 5,206,028 (i.e., containing unoriented short fibers) had both low suture retention strength and low tensile strength in two perpendicular directions.

TABLE 1

Physical Properties of Various Membranes

| Test | Membrane prepared from Example 3 (unoriented, long fibers) | Membrane prepared from Example 4 (unoriented, long fibers) | Membrane prepared according to U.S. Pat. No. 6,391,333 (oriented fibers) | Membrane prepared according to U.S. Pat. No. 5,206,028 (unoriented, short fibers) |
|---|---|---|---|---|
| Thickness (mm) | 0.26 ± 0.01 | 0.14 ± 0.01 | 0.26 ± 0.01 | 0.19 ± 0.002 |
| Density (g/cm³) | 0.36 ± 0.02 | 0.63 ± 0.09 | 0.42 ± 0.03 | 0.67 ± 0.10 |
| Hydrothermal transition temp. (° C.) | 55 ± 0.4 | 59 ± 0.2 | 56 ± 0.6 | 54.8 ± 1.0 |
| Suture retention strength (kg) | | | | |
| X-axis | 0.25 ± 0.10 | 0.32 ± 0.05 | N/A | 0.13 ± 0.02 |
| Y-axis | 0.26 ± 0.11 | 0.32 ± 0.11 | | |
| Tensile strength (kg/cm²) | | | | |
| X-axis | | 87 ± 20 | 79 ± 27 | N/A | 33.6 ± 6.10 |
| Y-axis | | 71 ± 3 | 68 ± 25 | | |

TABLE 1-continued

Physical Properties of Various Membranes

| Test | Membrane prepared from Example 3 (unoriented, long fibers) | Membrane prepared from Example 4 (unoriented, long fibers) | Membrane prepared according to U.S. Pat. No. 6,391,333 (oriented fibers) | Membrane prepared according to U.S. Pat. No. 5,206,028 (unoriented, short fibers) |
|---|---|---|---|---|
| Suture retention strength (kg) | | | | |
| Parallel to fiber orientation | N/A | N/A | 0.19 ± 0.03 | N/A |
| Perpendicular to fiber orientation | | | 0.27 ± 0.03 | |
| Tensile strength (kg/cm$^2$) | | | | |
| Parallel to fiber orientation | N/A | N/A | 82.1 ± 12.7 | N/A |
| Perpendicular to fiber orientation | | | 39.5 ± 6.4 | |
| Permeability to carbonic anhydrase (MW 29,000) (%) | 11 | 2.5 ± 2.3 | 2.8 ± 0.8 | Non-permeable |

Results are expressed as average of 5 measurements ± S.D.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of making an isotropic layer of cross-linked biopolymeric fibers, comprising:
    coacervating biopolymeric fibers having lengths of less than 1 cm dispersed in an aqueous solution to obtain coacervated biopolymeric fibers having lengths of 10 to 1,000 cm;
    mechanically compressing the coacervated biopolymeric fibers into a layer;
    air-drying or freeze-drying the layer such that the layer has a density of 0.1 to 1.2 g/cm$^3$; and
    cross-linking the biopolymeric fibers.

2. The method of claim 1, further comprising dehydrating the coacervated biopolymeric fibers to reach a solid content of 5-25 wt % before the mechanically compressing step.

3. The method of claim 2, wherein the biopolymeric fibers are collagen-based fibers.

4. The method of claim 3, wherein the biopolymeric fibers are 30 to 800 cm in length.

5. The method of claim 4, wherein the biopolymeric fibers are 50 to 500 cm in length.

6. The method of claim 1, wherein the biopolymeric fibers are collagen-based fibers.

7. The method of claim 6, wherein the biopolymeric fibers are 30 to 800 cm in length.

8. The method of claim 7, wherein the biopolymeric fibers are 50 to 500 cm in length.

9. The method of claim 1, wherein the biopolymeric fibers are 30 to 800 cm in length.

10. The method of claim 9, wherein the biopolymeric fibers are 50 to 500 cm in length.

* * * * *